United States Patent [19]

Nishimura

[11] Patent Number: 4,499,493
[45] Date of Patent: Feb. 12, 1985

[54] MULTIPLE MEASUREMENT NOISE REDUCING SYSTEM USING ARTIFACT EDGE IDENTIFICATION AND SELECTIVE SIGNAL PROCESSING

[75] Inventor: Dwight G. Nishimura, Palo Alto, Calif.

[73] Assignee: The Board of Trustees of the Leland Stanford Junior University, Stanford, Calif.

[21] Appl. No.: 468,656

[22] Filed: Feb. 22, 1983

[51] Int. Cl.³ .................... H04N 5/32; H04N 1/40
[52] U.S. Cl. ........................ 358/111; 358/282; 358/284; 378/92; 378/99; 364/414; 128/653
[58] Field of Search .............. 358/93, 111, 36, 167, 358/282, 284; 378/92, 97, 99, 115; 364/414; 128/653, 659

[56] References Cited

U.S. PATENT DOCUMENTS 4,445,226  4/1984  Brody ................................. 378/99
4,463,375  7/1984  Macovski ........................... 358/111

Primary Examiner—Howard W. Britton
Assistant Examiner—John K. Peng
Attorney, Agent, or Firm—Flehr, Hohbach, Test, Albritton & Herbert

[57] ABSTRACT

Disclosed is a multiple measurement multiple energy X-ray imaging system in which a plurality of measurements are processed to provide a first image signal representing a desired parameter of an object and in which the plurality of measurements are processed to provide a second processed image signal having greater signal-to-noise ratio than the first processed image signal but in which extraneous artifacts may be introduced into the signal. The spatial location of edges of the extraneous artifacts are determined. The first processed image signal and the second processed image signal are combined to provide an improved image signal except at the spatial locations of the extraneous artifacts where the first processed image signal is used for the image signal thereby eliminating the extraneous artifact from the displayed image.

14 Claims, 4 Drawing Figures

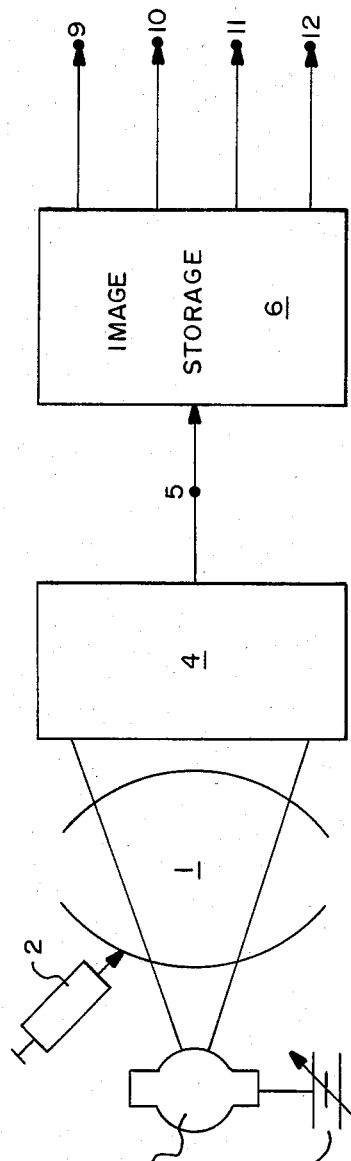
FIG.—1
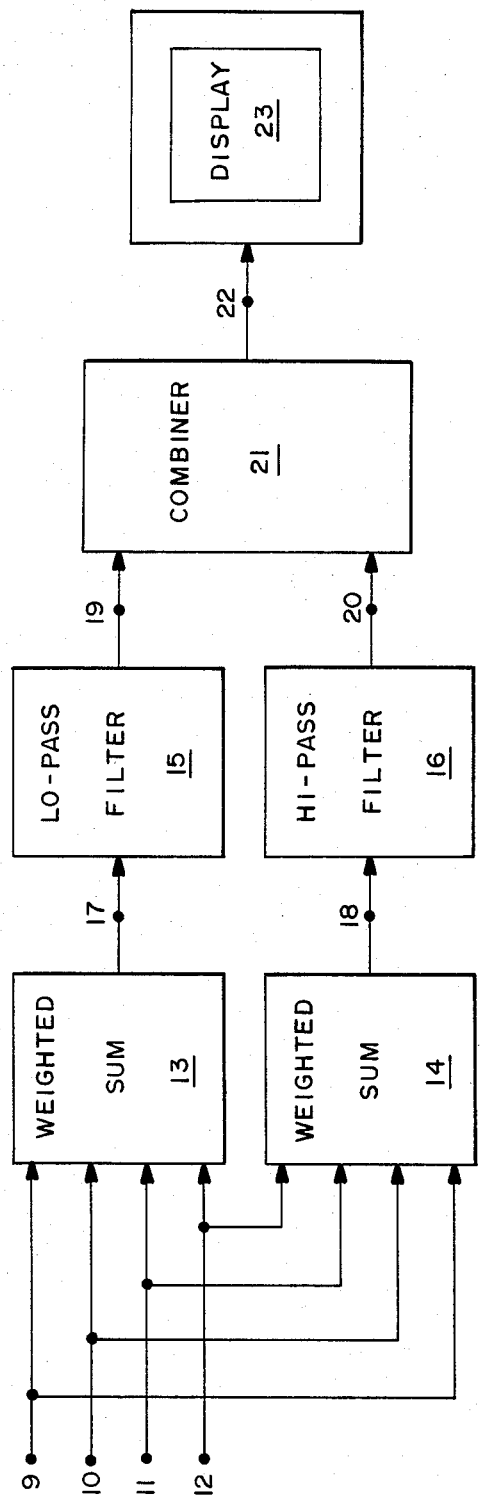
FIG.—2

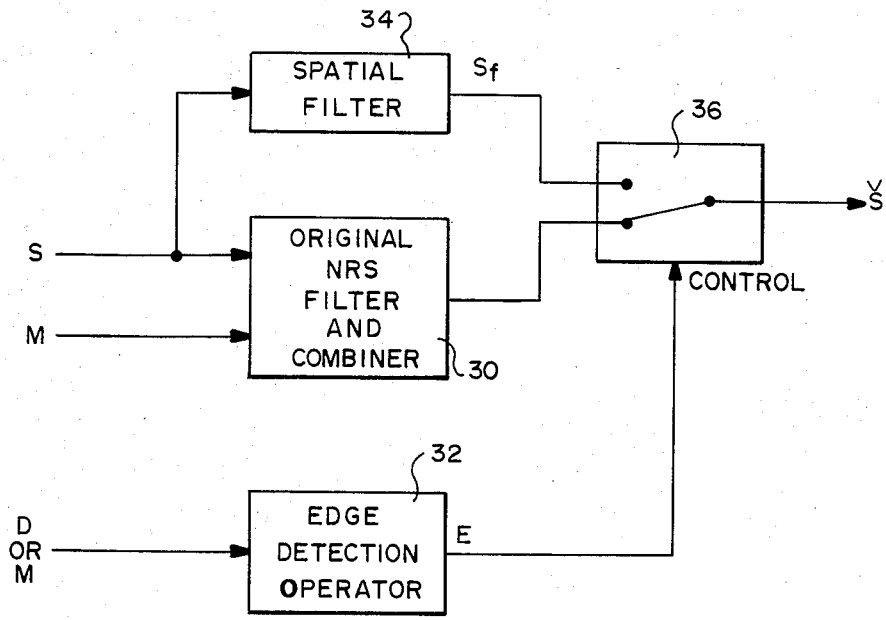
FIG.—3
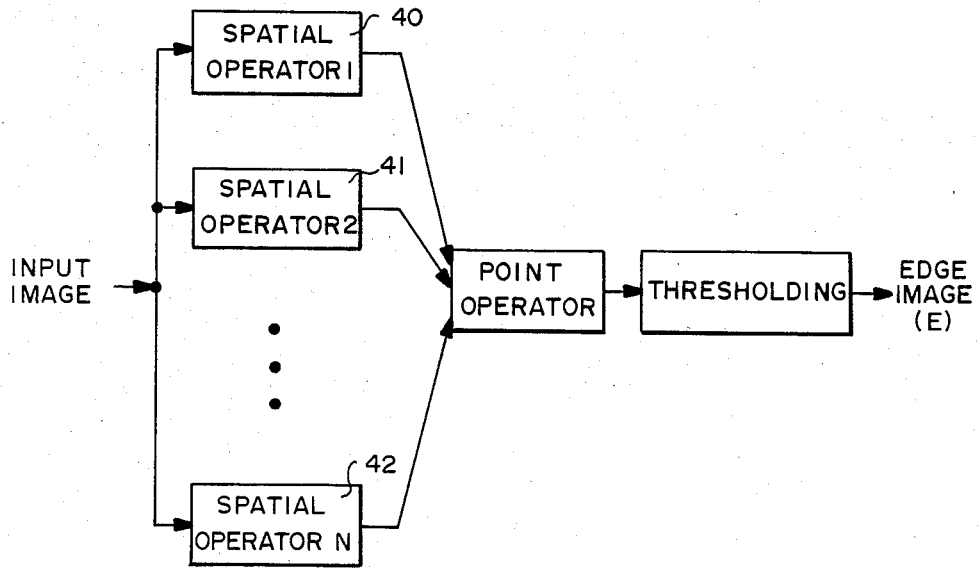
FIG.—4

MULTIPLE MEASUREMENT NOISE REDUCING SYSTEM USING ARTIFACT EDGE IDENTIFICATION AND SELECTIVE SIGNAL PROCESSING

This invention relates generally to imaging systems such as X-ray systems, and more particularly the invention relates to the processing of images derived from a plurality of measurements.

In many imaging application areas, images are constructed as a weighted sum of a plurality of measurements. A prime example is the recent new developments in X-ray imaging. Here measurements are made at different energies and/or at different times. These measurements are then combined to provide selective images representing specific materials.

One example is that of temporal subtraction techniques using digital radiography as described in the publication by C. A. Mistretta and A. B. Crummy, "Diagnosis of Cardiovascular Disease by Digital Subtraction Angiography," in *Science*, Vol. 214, pp. 761-65, 1981. Here measurements taken before and after the administration of iodine into blood vessels are subtracted to provide an image of vessels alone. Another example is that of energy-selective radiography as described in the publication by L. A. Lehmann, et al., "Generalized Image Combinations in Dual KVP Digital Radiography," in *Medical Physics*, Vol. 8, pp. 659-67, 1981. Here measurements made at different energies are combined to enhance or eliminate specific materials. A third example is energy-selective computerized tomography as described in the publication by R. E. Alvarez and A. Macovski, "Energy-Selective Reconstructions in X-ray Computerized Tomography," in *Physics in Medicine & Biology*, Vol. 21, pp. 733-744, 1976. Here sets of measurements are made at two energy spectra and distortion-free reconstructions are made which delineate the average atomic number and density of each region. A fourth example is hybrid subtraction described in U.S. application Ser. No. 260,694, filed May 5, 1981 and in the publication by W. R. Brody, "Hybrid Subtraction for Improved Intravenous Arteriography," in *Radiology*, Vol. 141, pp. 828-831, 1981. Here dual energy measurements are made before and after the administration of iodine. Each dual energy pair is used to eliminate soft tissue. In this way the resultant subtracted vessel images are immune to soft tissue motion.

In each case, where a number of measurements are combined to select specific material properties, the resultant SNR Signal-to-noise ratio) is reduced as compared to the nonselective image. Therefore, these various processing techniques which improve the visualization of disease processes by selecting specific materials have the disadvantage of a reduction in SNR. This reduced SNR can interfere with the ability to visualize regions of disease.

A system to improve the SNR of the hybrid subtraction and other multiple measurement systems has been developed by A. Macovski and is disclosed in U.S. patent application Ser. No. 415,334 filed Sept. 7, 1982 for "Multiple Measurement Noise Reducing System." An array of measurements are taken of an object under different conditions. These are combined to select a specific aspect of the object. The same measurements are then combined in different weightings to provide a lower-noise image, without the desired selectivity. The improved selective image is formed by combining the selective image with the lower-noise image using the lower frequency components of the former and the higher frequency components of the latter. To assure the proper ampltitude of the higher frequency components, the components are weighted such as with the ratio of the derivative of the selective image to the derivative of the lower-noise image. Nonlinear thresholds are used for those cases where this ratio becomes an unreliable indicator of the correct amplitude of the high frequency components. One limitation of the Macovski system is the introduction of extraneous signals (herein termed "artifacts") by the low noise signal.

The present invention is directed to an improvement in the Macovski system. The improvement eliminates severe artifact edges which may not otherwise be suppressed in the Macovski system. Briefly, the locations of the artifact edges in the image signal are identified and the display signal is switched from the Macovski noise-reducing system (NRS) signal to the initial selective signal, S, or a signal derived therefrom. In a preferred embodiment, the artifact edges are identified by passing an artifact image signal through a plurality of derivative operators in the horizontal and vertical directions to provide the two components of the spatial gradient vector, then taking the magnitude of the gradient at each point. This magnitude is then applied to a threshold detector. Since severe edges are of interest, a relatively large threshold is used. When the threshold is exceeded, thereby indicating a severe artifact edge in the NRS signal, the selective signal, S, or a signal derived therefrom is applied to the display.

Accordingly, an object of the present invention is a multiple measurement noise reducing system in which severe artifacts are eliminated.

Another object of the invention is a method of improving the image in a multiple measurement noise reducing system.

A feature of the invention is the detection of artifact edge locations in an image signal and switching to a signal not having the artifacts at the detected locations.

The invention and objects and features thereof will be most readily apparent from the following description and appended claims when taken with the drawings, in which:

FIG. 1 is a block diagram of an X-ray system for acquiring signals useful in the invention.

FIG. 2 is a block diagram of an X-ray system in accordance with the prior art.

FIG. 3 is a functional block diagram of an X-ray signal processing system in accordance with the present invention.

FIG. 4 is a functional block diagram of edge detection circuitry useful with the system of FIG. 3.

Referring now to the drawings, FIG. 1 is a block diagram of an X-ray system which includes an X-ray tube 8 supplied by variable voltage power source 3. The X-rays are transmitted through object 1, normally the human anatomy. The transmitted rays are received by X-ray detector 4, such as an image intensifier and television camera, or a one- or two-dimensional array of scintillators, etc. The image signal 5 is applied to storage system 6 where a plurality of images 9, 10, 11, 12, etc., can be stored.

In temporal subtraction a first image 9 is stored. Following adminstration of a contrast agent using syringe 2, a second image 10 is stored. These are then used in the subsequent processing systems. In energy selective systems, images 9, 10, 11, 12, etc., are stored at different values of beam energy corresponding to different anode voltages 3. In dual-energy systems, two voltages are used. In addition different X-ray beam filters, not shown, can be added.

In the Brody hybrid subtraction system previously described, measurements at two voltages are taken prior to the adminstration of contrast material. These are stored as 9 and 10. Following administration of the contrast agent, two additional measurements at the same two voltages are taken and stored as 11 and 12. These four measurements are then processed to obtain a low-noise image of the vessels opacified by the contrast material from syringe 2.

Referring now to FIG. 2, the lines 9, 10, 11 and 12 representing an array of X-ray measurements of an object, are processed in accordance with the Macovski system described above. These signals could be obtained, for example, from the output of the television camera in a fluoroscopic system where an array of images are formed and stored, for example, on a magnetic disc or in a solid-state frame memory. These signals can represent X-ray images taken with different photon energy spectra or taken before and after the administration of a contrast agent.

In general the multiple measurements are taken so as to provide the isolation or elimination of specific materials. One simple example involves the isolation of vessel images by subtracting measurements taken before and after the administration of an iodinated contrast agent. Other examples include measurements at different X-ray photon energy spectra which are then combined to eliminate or enhance specific materials.

Weighted summer 13 takes the measurements and provides selective signal 17, containing the desired material properties. Unfortunately, however, signal 17 often has relatively poor SNR. The weighted sum usually involves negative weights which diminish the signal. The noise variances of each independent measurement add, however, to provide a large variance, hence a low SNR. This SNR is considerably improved using low pass filter 15 which reduces the bandwidth. This noise reduction, however, is accomplished at the price of reduced resolution. A primary objective of this invention is to restore the resolution using a source of high frequency information with reduced noise.

Signals 9, 10, 11 and 12 are also applied to weighted summing structure 14. These weights can be chosen to maximize the signal-to-noise ratio for a particular component of the image. For example, for vessel imaging they can be chosen to maximize the signal-to-noise ratio for the iodinated contrast agent. This is in sharp distinction to weighted summing structure 13 where the weights are chosen to isolate iodine and eliminate the various tissue components. Ideally, the weights which maximize the SNR will vary in different portions of the image, depending on the intervening tissue. Thus, the weights can be varied as the signals are scanned. However, for simplicity, the weights can be fixed to maximize the average SNR with relatively small degradation in performance.

The high SNR weighted-sum signal, 18, is applied to high pass filter 16 which extracts the high frequency components. A preferred embodiment of this high pass filter is the complement of low pass filter 15. Thus the sum of the normalized transmissions equals unity within the frequencies of interest. These filters can either be implemented in the frequency domain or as convolution functions.

Combiner 21 combines the low frequency image or signal 19 with the high frequency image or signal 20 to obtain the processed image 22 which is displayed in display 23. Since signal 19 is low noise because of the filtering, and signal 20 is low noise because of the weightings, the processed signal 22 is a low noise version of the desired signal, having the full bandwidth or resolution.

The degree of artifacts in the image can depend on the nature of the combiner 21. For simplicity, the combiner 21 can simply be an adder. Here the desired selected image will have the required low noise and high resolution. However, signal 20 contains the high frequency components of undesired structures. For example, in vessel images, signal 20 contains the edges of undesired structures such as bone and various soft tissue organs and motion artifacts. Since these are only edges, however, a trained radiologist can ignore them and concentrate on the vessels.

This system is particularly applicable to the previously-described hybrid subtraction scheme. Assume summer 13 weights the four signals to eliminate everything but iodine, while also subtracting soft tissue motion artifacts. Summer 14 can, for example, weight the signals to provide a low noise temporal subtraction, without concern about soft tissue motion artifacts. This can be accomplished by using a large positive weight for the low energy signal before iodine is administered, and a smaller positive weight for the high energy signals since it contains less of the iodine component. These weights are reversed for the measurements taken after the iodine administration to provide a temporal subtraction of everything except iodine.

In this case, in the absence of motion, when 19 and 20 are added, the desired isolated vessel signal will be formed having its full resolution. In the presence of soft tissue motion, signal 19 will be immune and continue to be vessels only, as described in the previously referenced application on hybrid subtraction. Low noise signal 20, however, will contain motion artifacts. Thus when they are added in combiner 21, the edges of these artifacts will be present.

In accordance with the present invention, the multiple measurement noise reducing system of Macovski is modified whereby severe artifact edges, which may not be reliably prevented in the Macovski system, are eliminated by switching to the parameter selective signal or a signal derived therefrom in the image regions where the severe artifact edge is present.

Apparatus in accordance with the invention is illustrated in the block diagram of FIG. 3. The selective signal, S, 17 and the low noise signal, M, 18 ar applied to the NRS filter and combiner shown generally at 30 and which correspond to the functional elements 15, 16, and 21 in FIG. 2. The low noise signal, M, or a signal, D, which is the difference (M−S) or any other signal which includes the artifact, is applied to an edge detection operator 32 which identifies artifact edges and generates a signal, E, in response thereto. The signal E is applied to a switch 36 whereby the signal from the NRS filter and combiner 30 is overridden upon detection of an artifact edge, and the selective signal, S, or a spatially filtered version thereof derived from the spatial filter 34, is applied as the output image signal, Ŝ. Accordingly, in the region of the artifact edge, as identified by the edge detection operator, the artifact generated in the NRS filter and combiner 30 is eliminated by disconnecting the NRS filter and combiner.

FIG. 4 is a functional block diagram of one embodiment of an edge detector operator 32 of FIG. 3 and includes a plurality of derivative operators (or other edge filters) 40, 41, and 42, each receiving the input image signal, D or M, in the horizontal and vertical directions to provide the two components of the spatial gradient vector. The magnitude of the gradient vector at each point in the image signal as derived by the point operator 44 is then compared with a threshold. Other edge map techniques can be employed such as template filters known in the art to detect edge orientation and strength.

There has been described an improved multiple measurement noise reducing system in which the presence of severe artifacts is eliminated by detecting the presence of artifacts and selectively overriding the noise reduction system (NRS). By detecting the edges of an artifact through use of spatial operators and then selecting between the NRS signal and a higher noise or slightly distorted signal without artifacts, an improved image is provided. While the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

What is claimed is:

1. In an imaging system, apparatus for reducing extraneous image signals in a processed image signal of an object representing a desired parameter derived from a plurality of measurements comprising:

first processing means for processing said plurality of measurements and producing a first processed image signal representing said desired parameter, second processing means for processing said plurality of measurements and producing a second processed image signal having a greater signal-to-noise ratio from said first processed image signal, third processing means interconnected with said first processing means and said second processing means for receiving and combining said first processed image signal and said second processed image signal and producing a third processed image signal, means for determining the spatial location of edges of extraneous images in said second processed image signal, and means for switching from said third processed image signal to a signal based on said first processed image signal when edges of extraneous images are detected.

2. Apparatus as defined by claim 1 wherein said means for determining the spatial location of edges includes differential means for determining the components of the spatial gradient signal vector of the difference between the said first processed image signal and said second processed image signal.

3. In an imaging system, apparatus for reducing extraneous image signals in a processed image signal of an object representing a desired parameter derived from a plurality of measurements comprising:

first procssing means for processing said plurality of measurements and producing a first processed image signal representing said desired parameter, second processing means for processing said plurality of measurements and producing a second processed image signal having a greater signal-to-noise ratio from said first processed image signal, first filter means for receiving and low pass filtering said first processed image signal, second filter means for receiving and high pass filtering said second processed image signal, means for combining said filtered first processed image signal and said filtered second processed image signal to produce a combined image signal, means for determining the spatial location of edges of extraneous images in said second processed image signal, and means for switching from said combined image signal to a signal based on said first processed image signal in response to detection of edges of extraneous images.

4. Apparatus as defined by claim 3 wherein said means for determining the spatial location of edges includes differential means for determining the components of the spatial gradient signal vector of the difference between said first processed image signal and said second processed image signal.

5. Apparatus as defined by claim 3 wherein said first filter means and said second filter means are complementary in frequency.

6. Apparatus as defined by claim 3 wherein said first processed image signal is derived from a first weighted sum of said measurements and said second processed image signal is derived from a second weighted sum of said measurements.

7. Apparatus as defined by claim 6 wherein said imaging system comprises an X-ray system and said measurements are at different X-ray energies.

8. Apparatus as defined by claim 6 wherein said imaging system comprises an X-ray system and said measurements are at different times.

9. For use in an X-ray imaging system in which a plurality of measurements are made, a method of reducing extraneous signals in a processed image signal comprising the steps of:

processing said plurality of measurements to provide a first processed image signal representing a desired parameter of an object, processing said plurality of measurements to provide a second processed image signal having greater signal-to-noise ratio than said first processed signal and introducing artifact images, combining said first and second processed image signals and thereby providing a third processed image signal, determining the spatial location of edges of said artifacts in said second processed signal, and switching from said third processed image signal to said first processed image signal at the spatial location of said artifacts.

10. For use in an imaging system in which a plurality of measurements are made, a method of reducing extraneous signals in a processed image signal of an object comprising the steps of:

processing said plurality of measurements to provide a first processed image representing a desired parameter of said object, processing said plurality of measurements to provide a second processed image signal having greater signal-to-noise ratio than said first processed signal and introducing artifacts, low pass filtering said first processed image signal to reduce its noise, high pass filtering said second processed image signal, said high pass filtering being complementary to said low pass filtering, combining said filtered first processed image and said filtered second processed image to provide an improved processed image signal, determining the spatial location of edges of said artifacts, and selectively switching from said improved processed image signal to a signal based on said first processed image signal at the spatial locations of artifacts.

11. The method as defined by claim 10 wherein said step of determining the spatial location of extraneous artifact edges include determining the components of the spatial gradient signal vector of the difference between said first processed image signal and said second processed image signal.

12. The method as defined by claim 10 wherein said first processed image signal is derived from a first weighted sum of said measurements and said second processed image signal is derived from a second weighted sum of said measurements.

13. The method as defined by claim 10 wherein said imaging system comprises an X-ray system and said measurements are at different X-ray energies.

14. The method as defined by claim 10 wherein said imaging system comprises an X-ray system and said measurements are at different times.

* * * * *

UNITED STATES PATENT AND TRADEMARK OFFICE
CERTIFICATE OF CORRECTION

PATENT NO. : 4,499,493

DATED : February 12, 1985

INVENTOR(S) : DWIGHT G. NISHIMURA

It is certified that error appears in the above-identified patent and that said Letters Patent is hereby corrected as shown below:

Column 1, line 7, after the title, insert the following paragraph:

--This invention was made with Government support under contract N01-HV-02922 awarded by the National Institutes of Health. The Government has certain rights in this invention.--

Signed and Sealed this

Ninth Day of May, 1995

BRUCE LEHMAN

*Attest:*

*Attesting Officer*   *Commissioner of Patents and Trademarks*